United States Patent [19]
Szabo

[11] Patent Number: 5,214,066
[45] Date of Patent: May 25, 1993

[54] METHOD FOR PRODUCING AN ANIMAL MODEL FOR INFLAMMATORY BOWEL DISEASE INCLUDING ULCERATIVE COLITIS

[75] Inventor: Sandor Szabo, Brookline, Mass.

[73] Assignee: Brigham and Women's Hospital, Boston, Mass.

[21] Appl. No.: 510,229

[22] Filed: Apr. 18, 1990

[51] Int. Cl.$^5$ .................. A01N 43/36; A61K 31/40
[52] U.S. Cl. ........................ 514/423; 514/557; 514/628; 800/2; 435/172.1; 424/9
[58] Field of Search .............. 514/423, 628, 557; 800/2; 424/9; 435/172.1

[56] References Cited

PUBLICATIONS

Kilbey et al. (eds.) 1984 in: *Handbook of Mutogenicity Test Procedures* Second Edition. Elsevier, N.Y. pp. 485-494.
Szabo, S., *Am. J. Path.* 93:273-276 (1978).
Szabo, S. et al., *Science* 214:200-202 (1981).
Szabo, S. et al., *Drugs and Peptic Ulcer*, CRC Press, pp. 55-74 (1982).
Szabo, S. et al., *Gastroent.* 86:1271 (1984).
Szabo, S. et al., *Gastroent.* 87:228-229 (1984).
Szabo, S., *Digestive Diseases and Sciences* 30:28S-31S (1985).
Szabo, S. et al., *J. Pharm. Methods* 13:59-66 (1985).
Szabo, S. et al., *Gastroent.* 88:228-236 (1985).
Szabo, S. et al., *Scand. J. Gastroent.* 21 (Suppl. 125): 92-96 (1986).
Szabo, S. et al., *Toxicol. Path.* 16:205-212 (1988).
Szabo, S. et al., *Digestive Diseases and Sciences* 34: 1323 (1989).
Dupuy, D. et al., *Ulcer Diseases: New Aspects of Pathology and Pharmacology*, CRC Press, pp. 421-434 (1989).
Satoh, H. et al., *Gastroent.* 98:A202 (1990).
Beeken, W. L., "Experimental Inflammatory Bowel Disease" in: Kirsner, J. B., et al., eds., *Inflammatory Bowel Disease*, Lea and Febiger, Philadelphia, pp. 37-49 (1988).
Benitz, K. F. et al., *Fd. Cosmet. Toxicol.* 11:565-575 (1973).
Berger, R. L. et al., *Annals of Surgery* 152:266-273 (1960).
Engster, M. et al., *Toxicol. and Applied Pharm.* 38:265-282 (1976).
Ger, R. et al., *Dis. Col. & Rect.* 29:177-181 (1986).
Krasna, I. H. et al., *J. Ped. Surgery* 21:26-29 (1986).
Morris, G. P. et al., *Gastroent.* 96:795-803 (1989).
Onderdonk, A. B. et al., *Am. J. Clin. Nut.* 32:258-265 (1979).
Onderdonk, A. B., *Digestive Diseases and Sciences* 30 (Dec. Suppl.):40S-44S (1985).
Strober, W., *Digestive Diseases and Sciences* 30 (Dec. Suppl.):3S-10S (1985).
von Ritter, C. et al., *Gastroent.* 95:651-656 (1988).
von Ritter, C. et al., *Gastroent.* 96:811-816 (1989).

*Primary Examiner*—Christopher S. F. Low
*Attorney, Agent, or Firm*—Sterne, Kessler, Goldstein & Fox

[57] ABSTRACT

A new animal model for Inflammatory Bowel Disease, including idiopathic ulcerative colitis and Chron's disease, as well as methods for producing such as an animal, is provided. Chronic ulcerative condition is induced by topical administration of a sulfhydryl blocker, such as N-ethylmaleimide or iodoacetamide, to the colon. The new animal model is useful for studying the pathogenesis of chronic ulcerative disease, and prevention and treatment thereof, and for evaluating drugs suspected of being useful in the treatment of same.

5 Claims, No Drawings

METHOD FOR PRODUCING AN ANIMAL MODEL FOR INFLAMMATORY BOWEL DISEASE INCLUDING ULCERATIVE COLITIS

FIELD OF THE INVENTION

This invention relates to an animal model useful for studying the early development and treatment of Inflammatory Bowel Disease, including ulcerative colitis and Crohn's disease, in mammals, particularly humans.

BACKGROUND OF THE INVENTION

Ulcerative colitis (UC) and Crohn's disease, the two major forms of idiopathic Inflammatory Bowel Disease (IBD) in humans, are widespread and poorly understood disorders (Kirsner, J. B., et al., eds., *Inflammatory Bowel Disease:* 3rd ed., Lea and Febiger, Philadelphia (1988); Goldner, F. H., et al., Idiopathic Inflammatory Bowel Disease, in Stein, J. H., ed., *Internal Medicine*, Little Brown & Co., Boston, pp. 369-380 (1990); Cello, J. P., et al.. Ulcerative Colitis, in Sleisenger, M. H., et al.. eds., *Gastrointestinal Disease: Pathophysiology Diagnosis Management*, W. B. Saunders Co., Philadelphia, p. 1435 (1989)). The separation of these idiopathic diseases of unknown etiology from other forms of colitis and ileitis caused by infectious agents, drugs, or the solitary rectal ulcer syndrome and collagenous colitis is not always respected in the literature (Riddell, R. H., ed., *Pathology of Drug-induced and Toxic Diseases*, Churchill Livingstone, New York (1982)). The diagnosis of IBD of known and unknown etiology is often not only difficult but almost impossible, e.g., during serious local complications such as hemorrhage, toxic dilation, perforation, inflammatory polyps and strictures (Riddell, R. H., ed., *Pathology of Drug-induced and Toxic Diseases*, Churchill Livingstone, New York (1982)).

The pathology of ulcerative colitis usually refers to a more superficial mucosal disease in contrast to Crohn's disease with its deep, often transmucosal involvement and fissures (Riddell, R. H., ed., *Pathology of Drug-induced and Toxic Diseases*, Churchill Livingstone, New York (1982); Morrison, B. C., et al.. eds., *Gastrointestinal Pathology*, 2d ed., London (1979); Fenoglio-Preiser, C. M., et al., eds., *Gastrointestinal Pathology: An Atlas and Text*, Raven Press, New York (1989); Goldman, H., et al., *Hum. Pathol.* 13:981-1012 (1982)). Ulcerative colitis typically involves the rectum and extends proximally without intervening uninvolved "skip" areas which are usually the hallmarks of Crohn's disease. The histologic features of active ulcerative colitis include, beside the superficial ulcers, infiltration by inflammatory cells (e.g., mainly lymphocytes, plasma cells, variable number of neutrophils, eosinophils and mast cells) involving extensively the lamina propria. Crypt abscesses, i.e., aggregates of neutrophils near and invading the crypt epithelium are reliable indicators of activity, while depletion of mucin in goblet cells is a less frequent finding.

Despite all the controversy, most of the pathologists accept as "rule of thumb that well-formed, sarcoid-like granulomas are not part of the spectrum of UC and that if these are present, an alternative explanation must be found" (Riddell, R. H., ed., Pathology of Drug-induced and Toxic Diseases, Churchill Livingstone, New York (1982)). Foreign-body giant cells and collection of a few histiocytes, however, are often present because of rupture of crypt abscesses and spilling of mucin into the submucosa and eliciting of cellular reaction. Noncaseating granulomas, on the other hand, are often present in gut segments from Crohn's disease which is often also called granulomatous colitis.

Active ulcerative colitis is usually followed by resolving or quiescent forms of the disease. Alternatively, in the fulminant form of ulcerative colitis the deep ulcers extend into the muscularis propria, and the acute and chronic inflammatory cells also involve the submucosa and the true muscular layer in the vicinity of ulcers.

The etiology and pathogenesis of idiopathic IBD, as the name implies, are poorly understood. Numerous theories, however, implicate genetic predisposition, environmental factors, infectious agents and immunologic alterations (Kirsner, J. B., et al.. eds., *Inflammatory Bowel Disease*, 3rd ed., Lea and Febiger, Philadelphia (1988); Zipser, R. D., ed., *Dig. Dis. Sci.*, 33 *Suppl.*:1S-87S (1988)). Previous understanding of the pathogenesis was limited to a three-stage process: (a) an irritant, which could be an immune process or infectious agent, activates (b) leukocytes which release enzymes such as proteases and inflammatory mediators such as histamine, serotonin and prostaglandins, and (c) these products cause edema, pain, heat and loss of function. However, as the overview of a recently held symposium on mediators of IBD concluded, this process is probably correct but it is far more complicated (Zipser, R. D., ed., *Dig. Dis. Sci.*, 33 *Suppl.*:1S-87S (1988)).

The initial cell and tissue injury does not have to be a massive insult as subtle biochemical reactions such as generation of free radicals are also sufficient to initiate irreversible cell damage, especially if combined with periods of ischemia and reflow. The final and most potent mediator of this toxicity appears to be the hydroxyl radical derived from the iron-catalyzed interaction between superoxide and hydrogen peroxide (Grisham, M. B., et al., *Dig. Dis. Sci.* 33 *Suppl.*:6S-15S (1988)).

A working hypothesis was thus recently proposed stating that transient ischemic episodes in the intestine initiate a cascade of self-perpetuating cycles of reactive oxygen metabolites and free radicals. Tissue damage may be indirectly aggravated through inflammation as neutrophils generate substantial amounts of oxygen metabolites (Grisham, M. B., et al., *Dig. Dis. Sci.* 33 *Suppl.*:6S-15S (1988)). This possibility is in agreement with very recent data obtained on 27 patients with ulcerative colitis, 10 with acute bacterial diarrhea, and 20 healthy volunteers. These data indicate that the oxidative free radical generating capacity of polymorphonuclear leukocytes was markedly enhanced in patients with active ulcerative colitis as compared with controls and patients in remission (Shiratora, Y., et al., *Digestion* 44:63-171 (1989)). These results indeed strongly suggest that increased free radical production by leukocytes could be related to the initial pathogenesis or aggravation of ulcerative colitis.

Results of studies performed during the last few years indicate that mediators of inflammation arise from cells other than leukocytes (Zipser, R. D., ed., *Dig. Dis. Sci.*, 33 *Suppl.*:1S-87S (1988)). Fibroblasts, smooth muscle and other cells release prostaglandins which modulate blood flow and intestinal motility. The vascular endothelium and macrophages seem to be the source of interleukin-1 (IL-1) which is involved in the production of fever, lymphopenia and many metabolic changes (Dinarello, C. A., *Dig. Dis. Sci.* 33 *Suppl.*:25S-35S (1988)). A very recent report described an enhanced production of IL-IB by mononuclear cells isolated from mucosa of patients with active ulcerative colitis (Mahida, Y. R., et al.. Gut 30:835-838 (1989)). On the other hand, mononuclear cells from both forms of IBD generated less IL-2 than controls. Furthermore, increased number of IL-2 responsive killer cells or exacerbated reactivity to IL-2 was found, especially in Crohn's disease, indicating that reactivity to IL-2 distinguishes IBD from control intestinal mononuclear cells (Kusugami, K., et al., *Gastroenterology* 97:1-9 (1989)). .

Other mediators of inflammation in IBD include enhanced production of platelet-activating factor (PAF) during active disease and inhibition by sulfasalazine and prednisolone (Eliakim, R., et al., *Gastroenterology* 95:1167-1172 (1988)). Results from human and experimental IBD indicate an enhanced synthesis of eicosanoids such as prostaglandins, thromboxanes and leukotrienes (Schumert, R., et al., *Dig. Dis. Sci.* 33 *Suppl.*:58S-64S (1988)). These products may not only be involved in the pathogenesis of IBD but may have diagnostic value and serve as therapeutic targets. Specifically, the raised concentration of prostaglandin E2 in rectal dialysis fluid from patients with ulcerative colitis may identify patients with a risk of relapse (Lauritsen, K., et al., *Gut* 29:1316-1321 (1988)), while selective inhibition of leukotrienes may be a therapeutic strategy to reduce inflammation in IBD (Schumert, R., et al., *Dig. Dis. Sci.* 33 *Suppl.*:58S-64S (1988); Goetzl, E. J., et al., *Dig. Dis. Sci.* 33 *Suppl.*:36S-40S (1988); Allgayer, H., et al., *Gastroenterology* 96:1290-1300 (1989)).

In addition to the established mediators, potential humoral mediators of inflammation may also be involved in the pathogenesis of IBD, e.g., tumor necrosis factor, growth factors, neuropeptides, lipoxins, and mast cell products (Zipser, R. D., ed., *Dig. Dis. Sci.*, 33 *Suppl.:IS-*87S (1988); Shanahan, F., et al., *Dig. Dis. Sci.* 33 *Suppl.*:41S-49S (1988); Nast, C. C., et al., *Dig. Dis. Sci* 33 *Suppl.*:50S-57S (1988); Mayer, E. A., et al., *Dig. Dis. Sci.* 33 *Suppl.*:71S-77S (1988)). It is also possible that not only the number of inflammatory cells and their products are changed, but the number of receptors increase, such as the increased neutrophil receptors for and response to the proinflammatory peptide formyl-methionyl-leucyl-phenylalanine (FMLP) (Anton, P. A., et al., *Gastroenterology* 97:20-28 (1989)) and the adherence of leukocytes (Cason, J., et al., *J. Clin. Pathol.* 41:241-246 (1988)) in Crohn's disease.

The immunology of IBD remains a tantalizing and frustrating field (Hodgson, H. J. F., et al., *Balliere's Clin. Gastroenterol.* 1:531-542 (1987)). Despite very intensive investigations in patients and animal models of IBD, the basic question cannot be answered, i.e., whether ulcerative colitis and Crohn's disease are primarily manifestations of disordered immunity, or whether the immunologic abnormalities documented in idiopathic IBD secondary epiphenomena are generated during the process of disease (Hodgson, H. J. F., et al., *Balliere's Clin. Gastroenterol.* 1:531-542 (1987); Elson, C. O., The immunology of inflammatory bowel disease, in: Kirsner, J. B., et al., eds., *Inflammatory Bowel Disease*, Lea and Febiger, Philadelphia, pp. 97-164 (1988); MacDermott, R. P., et al., *Adv. Exp. Med. Biol.* 216A:3-35-344 (1987)). If the second possibility is correct, the nature of etiologic agent initiating the early cell and tissue injury remains unknown, and in addition, environmental and dietary factors as well as transmissible infectious agents should be considered (Calkins, B. M., et al., *Epidemiol. Rev.* 8:60-85 (1986); Myren, J., et al., *Scand. J. Gastroenterol.* 23 *Suppl.*:11-19 (1988); Mendelhoff, A. I., et al., The epidemiology of idiopathic inflammatory bowel disease, in Kirsner, J. B., et al., eds., *Inflammatory Bowel Disease*, Lea and Febiger, Philadelphia, pp. 3-34 (1988); Hodgson, H. J. F., et al., *Balliere's Clin. Gastroenterol.* 1:531-542 (1987); Elson, C. O., The immunology of inflammatory bowel disease, in: Kirsner, J. B., et al.. eds., *Inflammatory Bowel Disease*, Lea and Febiger, Philadelphia, pp. 97-164 (1988); MacDermott, R. P., et al., *Adv. Exp. Med. Biol.* 216A:3-35-344 (1987)). With these open dilemmas, immunologic studies of IBD have been concentrated on mechanisms that may be responsible for inflammation, irrespective of whether the pathogenesis of IBD has been initiated for immunologic reasons or in response to infection or other toxic agents (Hodgson, H. J. F., et al., Balliere's Clin. Gastroenterol. 1:531-542 (1987)).

The immunologic alterations in IBD are primarily autoimmune in nature, with colonic autoantibodies and lymphocyte-cytotoxicity directed against colonic epithelial cells. The immune response initially directed against bacteria in the gut could cross-react with intestinal epithelium due to antigenic similarity between these two targets. However, even the latest developments in the immunologic aspects of the pathogenesis of IBD cannot answer the basic question, i.e., whether the detected changes in humoral and cellular immunity reflect a primary defect or secondary response to injury.

Animal models are essential to study the etiology and pathogenesis of such a complex and probably multifactorial disease as idiopathic IBD. The criteria for an animal model of IBD and the insufficient quality and quantity of models have been reviewed repeatedly and extensively (Strober, W., *Dig. Dis. Sci.* 33 Suppl.:3S-1OS (1988); Beekan, W. L., Experimental inflammatory bowel disease, in: Kirsner, J. B., et al., eds., *Inflammatory Bowel Disease*, Lea and Febiger, Philadelphia, pp. 37-49 (1988)). The available animal models can be divided into naturally occurring and experimentally induced animal models. Unfortunately, only a few spontaneous and rarely occurring models of intestinal inflammation due to a genetic defect are available and most of these are not idiopathic but are induced by bacteria or other infectious agents (e.g., hyperplasia, crypt abscesses, ulcers in mice with *Bacillus psyliformnis* and hamster with "rod-shaped bacteria") (Strober, W., *Dig. Dis. Sci.* 33 *Suppl.*:3S-1OS (1988)). Rare forms of spontaneous ulcerative colitis and granulomatous enterocolitis also occur in rats and horses, respectively. Great expectations surrounded the initial reports on the potential use of marmosets and the cotton-top tamarin as a spontaneous model of ulcerative colitis and colonic adenocarcinomas (Clapp, N. K., et al., eds., *Dig. Dis. Sci.* 33 *Suppl.*:1S-158S (1988)). Unfortunately, multiple infections, the accompanying "wasting disease", the demanding conditions in husbandry and nutrition as well as the low survival rate (23-69%) of marmosets and tamarins contribute to the very limited availability of this grossly and microscopically good animal model of ulcerative colitis (Clapp, N. K., et al., eds., *Dig. Dis. Sci.* 33 *Suppl.*:1S-158S (1988)).

Experimentally induced animal models of ulcerative colitis are usually produced by exposure to toxic dietary substances, pharmacologic agents or other environmental chemicals, or by administration of materials derived from patients, or by manipulation of the animal's immune system (Strober, W., *Dig. Dis. Sci.* 33 *Suppl.*:3S-10S (1988); Beekan, W. L., Experimental inflammatory bowel disease, in: Kirsner, J. B., et al., eds., *Inflammatory Bowel Disease*, Lea and Febiger, Philadelphia, pp. 37-49 (1988); Onderdonk, A. B., *Dig. Dis. Sci.* 33 *Suppl.*:40S-44S (1988)). Although vascular changes, especially arterial occlusion and histamine administration, result in increased vascular permeability, mucosal necrosis and ulceration, the accompanying inflammation is very transient and cannot serve as a model of chronic ulcerative colitis (Beekan, W. L., Experimental inflammatory bowel disease, in: Kirsner, J. B., et al., eds., *Inflammatory Bowel Disease*, Lea and Febiger, Philadelphia, pp. 37-49 (1988); Krasna, I. H., et al., *J. Pediat. Surg.* 21:26-29 (1986)).

Neurogenic manipulation, especially the cholinergically induced hypermotility is also accompanied by limited colitis (Beekan, W. L., Experimental inflammatory bowel disease, in: Kirsner, J. B., et al., eds., *Inflammatory Bowel Disease*, Lea and Febiger, Philadelphia, pp. 37-49 (1988); Berger, R. L., *Ann. Surg.* 152:226 (1960)), and this might be an appropriate tool to study the stress-associated pathogenetic factors in ulcerative colitis (Szabo, S., *Dig. Dis. Sci.* 30 *Suppl.*:28S-31S (1985)). On the other hand, local administration of physical (e.g., hyperthermia) (Ger, R., et al., *Dis. Colon Rectum* 29:77-81 (986)) or chemical irritants (e.g., ethanol, acetic acid, formalin, detergents, hypertonic salt solutions and even nonsteroidal anti-inflammatory drugs) (Strober, W., *Dig. Dis. Sci.* 33 *Suppl.*:3S-10S (1988); Beekan, W. L., Experimental inflammatory bowel disease, in: Kirsner, J. B., et al., eds., *Inflammatory Bowel Disease*, Lea and Febiger, Philadelphia, pp. 37-49 (1988)) produce massive local tissue destruction which is often accompanied by very little or no inflammation. Furthermore, these nonspecific lesions usually heal relatively quickly and are not thus appropriate models of IBD.

Despite their limitations, the two most widely used models are the experimental colonic lesions produced by 2,4,6-trinitro-benzensulfonic acid (TNB) and carrageenan. Both models involve tissue destruction in the colon. Intrarectal administration of 5-30 mg of TNB in 0.25 ml of 50% ethanol in the rat produced dose-dependent colonic ulcers and inflammation which were maximal by gross and light microscopic examination at week, and by biochemical measurement of myeloperoxidase activity in the colon at 3-4 weeks (Morris, G. P., et al., *Gastroenterology* 96:795-803 (1989)). Histologically, the inflammatory infiltrate of mucosa and submucosa included polymorphonuclear leukocytes, lymphocytes, macrophages and connective tissue mast cells. Initially, massive edema and in the healing state (6-8 weeks) fibroblasts were also detected. Granulomas were seen in 57% of rats killed at 3 weeks.

In these experiments TNB acted as a hapten and ethanol apparently permitted its subepithelial penetration. Unfortunately, the TNB model is not reproducible without the nonspecific action of at least 30-40% ethanol (Morris, G. P., personal communication). Contrary to the results with rats, ethanol intake exerts a certain protection against IBD in humans. Furthermore, this rat model has been sensitive only to prevention (i.e., pretreatment) with 5-lipoxygenase inhibitors or leukotriene antagonists which, however, do not markedly influence the well developed state of disease (Morris, G. P., personal communication).

Carrageenan is a sulfated polygalactose (molecular weight above 100,000) widely used in the food industry and is considered safe for human use. Degraded forms of this polysaccharide (molecular weight 20,000-40,000) administered through drinking water induce ulcerative colitis in two weeks or later in experimental animals (Beekan, W. L., Experimental inflammatory bowel disease, in: Kirsner, J. B., et al., eds., *Inflammatory Bowel Disease*, Lea and Febiger, Philadelphia, pp. 37-49 (1988); Onderdonk, A. B., *Dig. Dis. Sci.* 33 *Suppl.*:40S-44S (1988); Benitz, K. F., et al., *Food Cosmet. Toxicol.* 11:565 (1973); Engster, M., et al., *Toxicol. Appl. Pharmacol.* 38:265 (1976)). In addition to ulcers, acute and chronic inflammation, macrophages laden with degraded carrageenan and suppressed phagocytosis are seen.

Carrageenan is toxic to monocytes and lymphocytes in vivo and after several days of culturing in vitro, and in vivo it enhances the lectin-dependent cellular cytotoxicity toward human cultured carcinoma cells (Beekan, W. L., Experimental inflammatory bowel disease, in: Kirsner, J. B., et al., eds., *Inflammatory Bowel Disease*, Lea and Febiger, Philadelphia, pp. 37-49 (1988)). A major advancement in the understanding of this experimental model of ulcerative colitis has been achieved after the recognition that *B. vulgatus* is required for the induction of carrageenan-induced colitis (Onderdonk, A. B., *Dig. Dis. Sci.* 33 *Suppl.*:40S-44S (1988); Onderdonk, A. B., et al., *Am. J. Clin. Nutr.* 32:285 (1979)). Furthermore, glandular atypism was noticed in rabbits on a 28-month study with carrageenan, and rats ingesting 1-10% carrageenan through diet develop colorectal adenomas and adenocarcinomas, providing thus an experimental link and tool to study the relationship of ulcerative colitis and carcinogenesis (Beekan, W. L., Experimental inflammatory bowel disease, in: Kirsner, J. B., et al., eds., *Inflammatory Bowel Disease*, Lea and Febiger, Philadelphia, pp. 37-49 (1988)). The carrageenan-induced colitis, however, exerts great variability in animal susceptibility and reproducibility, and requires several weeks or months for full development. In addition to carrageenan, the FMLP-induced experimental colonic lesions also represent a transition between chemically and cellularly induced animal models. This bacterial peptide activates and attracts neutrophils, and causes ulcers and inflammation in the rat ileum (VonRitter, C., et al., *Gastroenterology* 95:651-656 (1988); VonRitter, C., et al., *Gastroenterology* 96:811-816 (1989)). This new animal model, like the TNB, has not yet been extensively used.

SUMMARY OF THE INVENTION

This invention is directed to a new animal model for inflammatory bowel disease in mammals, particularly humans, including ulcerative colitis. Topical administration of sulfhydryl blockers such as N-ethylmaleimide and iodoacetamide in rodent colon induces chronic ulcerative colitis. The pathogenesis of chronic ulcerative colitis may be studied and protective drugs may be evaluated using this animal model.

DETAILED DESCRIPTION OF THE INVENTION

This invention relates to a new animal model for IBD, including ulcerative colitis and Crohn's disease. The animal model involves treatment of rodents or other mammals with sulfhydryl (SH) blockers. Preferred SH blockers include N-ethylmaleimide (NEM)

and iodoacetamide (IA). The resulting colonic cell injury associated with treatment with these compounds produces an erosion and ulcer and the necrosis is accompanied by acute and chronic inflammation. This condition correlates well with Inflammatory Bowel Disease, particularly ulcerative colitis and Chron's disease, in mammals, particularly humans.

As used herein, "animal" refers to a laboratory animal such as rat, mouse, hamster, or guinea pig. Other suitable animals susceptible to experimentally-induced IBD may also be used. "Administering" refers to the treatment of an animal with a compound of the invention. As used herein, the compounds of the invention may be administered to the colon of the animal by use of a catheter. Other suitable means of introducing material into the colon may be known to those of skill in the art and these means are intended to be within the scope of the term "administering" as used herein. The term "sulfhydryl blocker" refers to a compound which is capable of alkylating protein sulfhydryl (SH) groups. Sulfhydryl blockers include the SH alkylators iodoacetamide and N-ethylmaleimide. Other compounds within the scope of the definition are iodoacetamine and chloroacetate. Further compounds include others which alkylate protein SH groups in cell membrane and cell adhesion molecules such as fibronectin and laminin.

The sulfhydryl blockers may be administered in compound form or as a part of a composition, said composition comprising the sulfhydryl blocker in combination with a pharmaceutically acceptable carrier. A typical carrier is methyl cellulose.

A preferred route of administration of the SH blockers is by catheter to deliver the compound directly to the colon. Most preferably, a rubber catheter such as a Nelaton catheter No. 8 is used (Rush Company, West Germany). The compound is preferably introduced about 6 cm from the rectum in the rat. One of skill in the art will be familiar with the use of such catheters to deliver compounds to the desired site in rats of varying ages and weights and in other experimental animals.

The animals treated with SH blockers as described above are then used for a variety of determinations to evaluate the development of ulcerative colitis. In an illustrative experiments, two groups of rats (control and experimental) are used, each having 3-5 rats. Each experiment is repeated at least once and the results are pooled.

The agents used to induce colonic lesions include the SH alkylators IA and NEM (Sigma Chemical Company, St. Louis, MO) which are solubilized in 1% methyl cellulose (Sigma Cat. No. 0512) at 0.3, 1,2,3,5 and 10% concentrations to be administered intercolonically (i.c.) in a volume of 0.1 ml about 6 cm from the rectum by rubber Nelaton catheter No. 8. During the experiments rats are clinically evaluated daily, and presence or absence of diarrhea is monitored. The animals are killed by decapitation between 1 hr and 60 days.

The organs to be studied (e.g., colon, segments of ileum, jejunum and, for comparison, duodenum, stomach, liver) are rapidly removed (within min), the colon weighed and either immediately placed into fixative or processed for biochemical studies or kept frozen for up to 2 weeks.

For morphologic studies at the light microscopy level 2-4 mm long tissue sections are fixed in 10% buffered (pH7) formalin, dehydrated and embedded in paraffin or in the J8-4 plastic embedding medium. Sections (1-5 um) from all organs are stained with hematoxylin and eosin (H&E) and, in addition, sections from stomach and duodenum are also stained with the periodic acid-Schiff (PAS) technique.

In pharmacologic experiments, detailed dose- and time-response studies are performed with potentially protective drugs which will also be administered by various routes (e.g., i.c., per-os (p.o.)). The colonic lesions are quantitated by computerized planimetry coupled with stereomicroscropy (Szabo, S., et al., *J. Pharm. Methods* 13:59-66 (1985)), and by a combination of damage score derived from gross and histologic examination of intestines, colonic weight and myeloperoxidase activity, as described by Morris et al. with the TNB model of IBD (Morris, G. P., et al., *Gastroenterology* 96:795-803 (1989)).

For biochemical studies, the tissue (total thickness, mucosa and muscle separated in certain experiments) is either homogenized with a Tekmar homogenizer, or kept frozen for up to two weeks.

For statistical evaluation, the results are stored and analyzed by computer. The statistical significance of differences of the group values are calculated (for parametric data) by two-tailed Student's t-test or (with parametric statistics) by the Mann-Whitney test or the Fisher-Yates Exact Probability Test.

Grossly and histologically the lesions produced by NEM or IA were similar. After initial diffuse swelling, edema and redness involving about 3-4 cm of the colon during the first 48 hours, single or usually multiple irregular ulcers (2-10 mm in diameter) were seen. If the lesions were large and deep, they usually were surrounded by serosal reaction and adhesion to surrounding structures. Perforations were rare but if present, the adhesions with adjacent organs were massive. Histologically, the initial massive edema involving the lamina propria and submucosa were followed by erosions and ulcers. The necrotic craters were surrounded mainly by polymorphonuclear leukocytes during the first 3-7 days, than predominantly by mononuclear lymphocytes, plasma cells and macrophages. Granulomas were usually not seen but collections of epithelial histiocytes surrounding a few multinucleated giant cells were occasionally observed. The acute and chronic inflammation usually involved the mucosa and submucosa, and rarely extended into the muscularis propria.

Using the new animal model described herein, it is now possible to evaluate the fine histological and cellular changes present at early stages of IBD. The model also allows development of therapeutic and preventive strategies. For the first time, therapy can be targeted directly to the site of the induced ulcer(s).

For example, using this new animal model of ulcerative colitis, it is possible to test the hypothesis that the healing of IBD is mainly influenced by angiogenesis and development of dense granulation tissue which will serve as a firm ground for re-epithelization to complete the recovery of mucosal defect. Preliminary morphometric results using bFGF treatment for experimental chronic duodenal ulcer (Szabo, S., et al., *Dig. Dis. Sci.* 34:1323 (1989)) and ulcerative colitis (Satoh, F. and Szabo, S., *Gastroenterology* (1990)) indicate that the capillary density of granulation tissue from rats treated with bFGF derivatives is 2- to 9-fold higher than in control animals. Furthermore, new biochemical data on the phosphorylation of bFGF and its control by fibronectin and laminin indicate new physiologic interactions between this growth factor and cell adhesion molecules (Feige, J. J., et al., *J. Cell. Biol.* 109:3105-3114 (1989)).

One of skill in the art will recognize the usefulness of this new animal model to evaluate factors involved in IBD development. For example, experimental protocols can be designed for evaluating the effect of dietary variations on IBD development and progression.

Other uses of the new animal model will be clear to one of skill in the art relating to IBD and will include evaluating development, progression, prevention and treatment of IBD. The new animal model will also be useful for evaluating and testing new theories of IBD causation and prevention as these theories become known in the art.

EXAMPLES

Example 1: Morphological Characterization

Materials.—IA and NEM (both obtained from Sigma Chemical Company, St. Louis, MO), were prepared as 0.3,1,2,3,5 and 10% solutions in 1% aqueous methyl cellulose and administered i.c. in volume of 0.1 ml by Nelaton rubber tube, to about 6 cm from the rectum. For the duration of per rectum administration, the rat will be placed into a Bollman type mildly restraining cage, the tail lifted and the rubber tube gently pushed up to about 6 cm from the rectum. After administration of 0.1 ml of solution, the tube is removed and the animal is released. Groups of animals are killed 1,4 hr, 2,7 and 21 days during the initial dose-response studies. Subsequently, a dose of IA and NEM are selected and full time-course studies run with autopsies 1,2,4,8,16,24 hr, 2 days, 5,7,14,21,40 and 60 days later. Certain groups of rats (i.e., those to be killed before 2 days) receive 3 minutes before autopsy under mild ether anesthesia 0.1 ml of the 3% suspension of monastral blue B to label damaged vascular endothelial cells in search of early vascular injury in the pathogenesis of this experimental IBD.

The animals are killed by decapitation, the colon rapidly removed, opened, rinsed in saline, blotted gently, weighed and fixed in 10% formalin. Standardized sections of ileum, jejunum, duodenum, stomach, liver, pancreas, kidneys and lungs are also fixed, and processed for histologic examination. Additional sections from grossly involved and uninvolved areas of colon, ileum and jejunum are frozen and subsequently homogenized for the determination of colonic myeloperoxidase activity by the method of Bradley et al. (Bradley, P. P., et al., *J. Invest. Dermatol.* 78:206-209 (1982)) using 0.0005% hydrogen peroxide as a substrate. This enzyme, located mainly in the azurophilic granules of polymorphonuclear leukocytes is used as a quantitative index of inflammation (Morris, G. P., et al., *Gastroenterology* 96:795-803 (1989); Bradley, P. P., et al., *J. Invest. Dermatol.* 78:206-209 (1982); Krawisz, J. E., et al., *Gastroenterology* 47:1344-1350 (1985)). In preliminary experiments with the chronic gastritis induced by 0.1% NEM (Szabo, S., et al., *Gastroenterology* 86:1271 (1984)), myeloperoxidase activity in the gastric mucosa was increased by 44% within 1 week, in correlation with the severity of inflammatory infiltrate.

Morphometric analysis of colonic lesions is performed by stereomicroscopic planimetry (Szabo, S., et al., *J. Pharm. Methods* 13:59-66 (1985); Szabo, S., et al., *Gastroenterology* 88:228-236 (1985); Szabo, S., et al., *Scand. J. Gastroenterol.* 21 *Suppl.*:92-96 (1986)). In addition, "damage scores" 0-5 are calculated using a combination of gross and histologic assessment of the extent of TNB-induced colonic lesions (Morris, G. P., et al., *Gastroenterology* 96:795-803 (1989)). Thus, there are four quantitative endpoints in evaluating the experimental colonic lesions: planimetry ($mm^2$) of involved colon, damaged score (grades 0-5) derived from gross and histologic evaluation, colon weight (Calkins, B. M., et al., *Epidemiol. Rev.* 8:60-85 (1986)) indicating edema, inflammatory infiltrate and tissue proliferation, as well as myeloperoxidase activity quantitatively reflecting the intensity of inflammation.

All the four endpoints have been found sensitive and quantitive indicators of the severity and extent of induced experimental gastric and colonic lesions (Szabo, S., et al., *Gastroenterology* 86:1271 (1984); Szabo, S., et al., *Dig. Dis. Sci.* 34:1323 (1989); Szabo, S., et al., *J. Pharm. Methods* 13:59-66 (1985); Morrison, B. C., et al., eds., *Gastrointenstinal Pathology*, 2d ed., London (1979); Szabo, S., et al., *Scand. J. Gastroenterol.* 21 Suppl.:92-96 (1986)).

For further characterization of chronic inflammation, standard immunoperoxidase and cytochemical methods are used to selectively obtain and count subpopulations of B and T-lymphocytes in the inflamed colon. The colons of rats which received the vascular tracer monastral blue for the detection of early vascular injury, which is well established in the pathogenesis of chemically induced gastric lesions (Szabo, S., et al., *Gastroenterology* 88:228-236 (1985); Szabo, S., et al., *Scand. J. Gastroenterol.* 21 *Suppl.*:92-96 (1986)), are cleared in glycerol for 24 hr after planimetric assessment of mucosal ulcers. The area of blood vessels labelled with deposition of monastral blue between the damaged endothelium and vascular basement membrane, are measured by stereomicroscopic planimetry (Szabo, S., et al., *Gastroenterology* 88:228-236 (1985); Szabo, S., et al., *Scand. J. Gastroenterol.* 21 *Suppl.*:92-96 (1986)).

Tissue samples from colon and ileum from rats killed up to 2 days after IA or NEM are fixed in Karnovsky's fixative for electron microscopy, dehydrated in graded ethanol, embedded, cut and stained for examination by transmission electron microscopy as described (Trier, J. S., et al., *Gastroenterology* 92:13-22 (1987)).

Example 2: Functional Studies

Methods.—To measure capillary blood flow, the laser-Doppler velocimeter is used as it was successfully applied in studies on rat stomach (Pihan, G., et al., *Gastroenterology* 91:1415-1426 (1986)). Briefly, the rat is anesthetized with pentobarbital (4.5 mg/100 g intraperitoneally (i.p.)) and following laparotomy, a segment of colon is isolated and a longitudinal incision is made by electrocautery (to minimize hemorrhage). The colonic mucosa is exposed and an aluminum disk with a central hole of 5 mm diameter is fixed to the serosal surface of the posterior wall of the colon with a water-resistant adhesive (Krazy Glue, Itasca, Ill.). This procedure is essential to immobilize completely the mucosal area to be observed through the microscope. Leakage of fluid from the chamber is prevented by interposing "silly putty" between the chamber and the mucosa (Guth, P. H., et al., *Am. J. Dig. Dis.* 17:391-398 (1972)). The chamber is filled with saline which is maintained at 37° C. by a warming coil inside the chamber. A Med-Pacific needle probe (100/500) with a spatial resolution in the tissue 0.5-1 mm is placed within 0.5 mm of the posterior mucosa. During surgery a 3-0 silk suture is placed around the subdiaphragmatic aorta proximal to the celiac artery to temporarily occlude the aorta (10–15 sec) to obtain a reading of zero blood flow in visible capillaries and collecting veins.

The probe is held vertically above the mucosal surface by the moving train of the microscope. A separation of about 0.5 mm between the tip of the probe and the mucosal surface does not interfere with obtaining the flow signal. After a stabilization period of 30 min in which the mucosal chamber was kept filled with saline, test solutions (e.g., doses of IA, NEM) are applied topically for 5 min. Changes in blood flow are estimated by integrating the tracings (area under the curve) in periods of 1 min after different exposure times using a microprocessor-linked planimeter and results are expressed as percentage of pretreatment control values. Baseline readings for zero blood flow are obtained at the beginning and end of each experiment by transient aortic occlusion. Fifteen minutes after withdrawal of the damaging agent, animals are killed and the colon immediately retrieved, fixed in formalin and processed for histologic examination.

The laser-Doppler method is the only one available for continuous measurement of blood flow and the detection of rapid changes in microcirculation, as compared to the hydrogen clearance technique which can demonstrate changes in blood flow only in 10–15 minutes due to the slow progression of tissue saturation with the gas (Pihan, G., et al., *Gastroenterology* 91:1415–1426 (1986); Guth, P. H., et al., *Am. J. Dig. Dis.* 17:391–398 (1972); Kile, J. W., et al., *Am. J. Physiol.* 249:G539–G545 (1985); Granger, D. N., et al., *Gastroenterology* 88:1073–1076 (1985); Bonner, R., et al. *App. Opt.* 20:2097–2107 (1981)).

Vascular permeability will be quantitated by measuring the extravasation into the colonic tissue of Evan's blue injected i.v. as described in studies with chemically induced lesions in the gastric mucosa (Szabo, S., et al., *Gastroenterology* 88:228–236 (1985); Szabo, S., et al., *Scand. J. Gastroenterol.* 21 Suppl.:92–96 (1986)). Briefly, groups of rats to be killed in the time-course experiments up to 2 days after i.c. administration of a medium damaging dose of IA or NEM, will receive Evan's blue i.v. 1 mg/100 g, 15 minutes before autopsy. Sections of colon and ileum will be removed, weighed and digested in 32% HCl. After organic and aqueous extraction, the concentration of Evan's blue is measured spectrophotometrically at absorbance 610 nm (Szabo, S., et al., *Gastroenterology* 88:228–236 (1985)).

Intestinal permeability is measured by the urinary excretion of polyethylene glycols of different molecular sizes administered into the small intestine or colon (Tagesson, C., et al., *Scand. J. Gastroenterol.* 18:481–486 (1983)). In a shortened time-course experiment, rats are anesthetized, 1,2,6 or 24 hr after a single medium dose of IA or NEM i.c. and 10 cm segment of the distal ileum or, in additional rats, colon is ligated and 1 ml of saline containing 300 mg of polyethylene glycol, 634–1338 daltons is injected through a plastic canula (1.4 mm in diameter). Urine is collected for 6 hr after catheterization of urethra. The urine is extracted and eluted with chloroform and methanol, evaporated, solubilized in deionized water, filtered and the concentrations of polyethylene glycols measured by reversed-phase HPLC.

Example 3: Biochemical Characterization

Methods.—Tissue samples are obtained from groups of rats killed up to 2 days after a single dose of IA or NEM in the morphologic time-course experiments. Initially, to obtain larger quantities of tissues, mucosal scrapings from 1–2 cm segments of ileum, jejunum, proximal and distal colon are obtained in similar time-course experiments but especially designed for these biochemical experiments. After weighing, tissues are homogenized in cold 0.2M perchloric acid, and after centrifugation, the supernatant is injected into a Bioanalytical Systems LC-154 HPLC with a dual gold mercury electrode to measure nonprotein glutathione and cysteine concentration (Dupuy, D., et al., *J. Liquid. Chromatography* 10:107–119 (1987)). Subsequently, the protein pellet is divided into two parts: one part after borohydride reduction and HPLC yields protein-bound glutathione and cysteine, while the other part of pellet following acid hydrolysis and HPLC indicates protein cysteine and cystine concentrations. The values from protein hydrolysate are compared with the spectrophotometric determination of total protein SH concentration using the Ellman's reagent (Szabo, S., et al., *Science* 214:200–202 (1981); Dupuy, D., et al., *J. Liquid. Chromatography* 10:107–119 (1987)).

Frozen tissue samples from these experiments may be used to measure fibronectin concentration by radioimmunoassay (Colvin, R. E., Fibronectin in wound healing, in: *Fibronectin*, Academic Press, pp. 213–254 (1989); Quaroni, A., et al., *Proc. Natl. Acad. Sci.* 75:5548–5552 (1978)).

We claim:

1. A method to produce mammalian idiopathic inflammatory bowel disease in a non-primate laboratory animal comprising topically administering to the colonic mucosa of the laboratory animal a composition comprising a sulfhydryl blocker in an amount effective to produce colonic lesions in said laboratory animal whereby the mammalian idiopathic inflammatory bowel disease is produced in the animal.

2. The method of claim 1, wherein said sulfhydryl blocker is chosen from the group consisting of N-ethyl-maleimide, iodoacetamide, iodoacetate or chloroacetate.

3. The method of claim 1, wherein said composition further comprises a pharmaceutically effective carrier.

4. The method of claim 3, wherein said carrier is methyl cellulose.

5. The method of claim 1 wherein said idiopathic Inflammatory Bowel Disease is ulcerative colitis or Crohn's disease.

* * * * *